(12) United States Patent
Hansson et al.

(10) Patent No.: US 6,486,140 B2
(45) Date of Patent: *Nov. 26, 2002

(54) AGENTS, AND METHODS EMPLOYING THEM, FOR THE PREVENTION OR REDUCTION OF TISSUE ADHESION AT A WOUND SITE

(75) Inventors: Hans-Arne Hansson, Hovås (SE); Gunilla Johansson-Rudén, Askim (SE); Olle Larm, Bromma (SE)

(73) Assignee: Medicarb AB, Bromma (SE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/412,869

(22) Filed: Oct. 5, 1999

(65) Prior Publication Data

US 2001/0056079 A1 Dec. 27, 2001

Related U.S. Application Data

(63) Continuation of application No. 08/513,777, filed as application No. PCT/SE95/00856 on Jul. 13, 1995, now abandoned.

(30) Foreign Application Priority Data

Jul. 19, 1994 (SE) .............................................. 9402529

(51) Int. Cl.⁷ ............................................ A61K 31/727
(52) U.S. Cl. ........................................... 514/55; 514/56
(58) Field of Search ...................................... 514/55, 56

(56) References Cited

U.S. PATENT DOCUMENTS

| 4,326,532 A | 4/1982 | Hammar | 128/349 R |
|---|---|---|---|
| 4,613,665 A | 9/1986 | Larm | 536/20 |
| 4,804,744 A | 2/1989 | Sen | 530/350 |
| 5,093,319 A | 3/1992 | Higham et al. | 514/55 |
| 5,116,824 A | 5/1992 | Miyata et al. | 514/55 |

FOREIGN PATENT DOCUMENTS

| RU | 353724 | 11/1972 |
|---|---|---|
| WO | 9013302 | 11/1990 |
| WO | 9209635 | 6/1992 |
| WO | 9305793 | 4/1993 |

OTHER PUBLICATIONS

Pitaru, et al., J. Periodontology 62:598–601 (1991).
Lossing, et al., Plastic and Reconstructive Surgery 91:1277–1286 (1993).
Kuettner, et al., J. Cell. Biochem. 27: 327–336 (1985).
Kleinman, et al., J. Cell. Biochem. 27: 317–328 (1985).
Grinnel, J. Cell. Biochem. 26: 107–116 (1984).
Aiba, et al., Biomaterials 8: 481–488 (1987).
Yamaguchi, et al., Agric. Biol. Chem. 42: 1297–1299 (1978).
Miki, et al., "Characterization of Human Cementum Growth Factor," Periodontal Research, p. 280, Abstract No. 1388 (1987).
Clark, et al., "Wound Repair," Chapter 10, pp. 197–262 (1985).
Pitaru, et al., "Collagen Membranes Prevent the Apical Migration of Epithelium . . . ," Oral and Maxillofacial Surgery/Perriodontal Research, p. 822, Absract No. 870 (1989).

*Primary Examiner*—James O. Wilson
*Assistant Examiner*—Leigh C. Maier
(74) *Attorney, Agent, or Firm*—White & Case LLP

(57) ABSTRACT

The use of chitosan and a polysaccharide immobilized thereto selected from heparin, heparan sulphate and dextran sulphate for the manufacture of an agent capable of preventing or substantially reducing undesirable adhesion of damaged tissue with adjacent or surrounding tissues in connection with wound healing; and a process for the use of such agent.

13 Claims, 1 Drawing Sheet

*Fig 1*

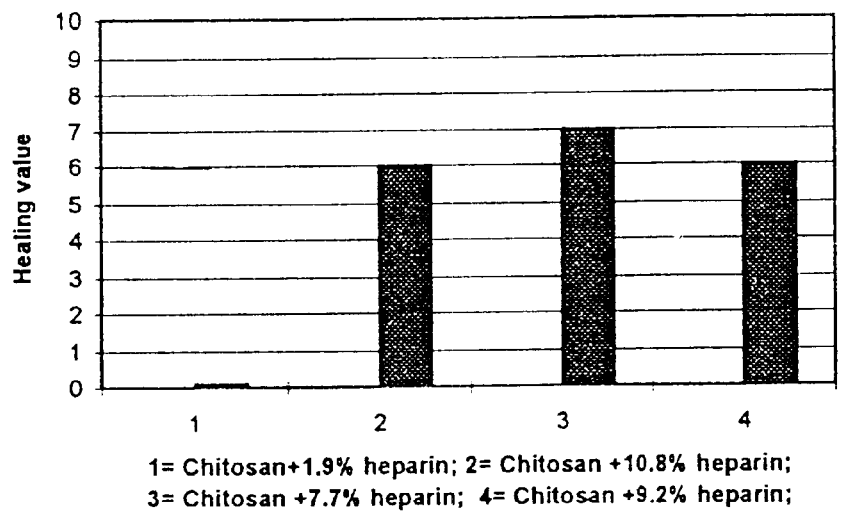

Healing of wounds after treatment with different heparin/ chitosan compositions

1= Chitosan+1.9% heparin; 2= Chitosan +10.8% heparin;
3= Chitosan +7.7% heparin; 4= Chitosan +9.2% heparin;

*Fig 2*

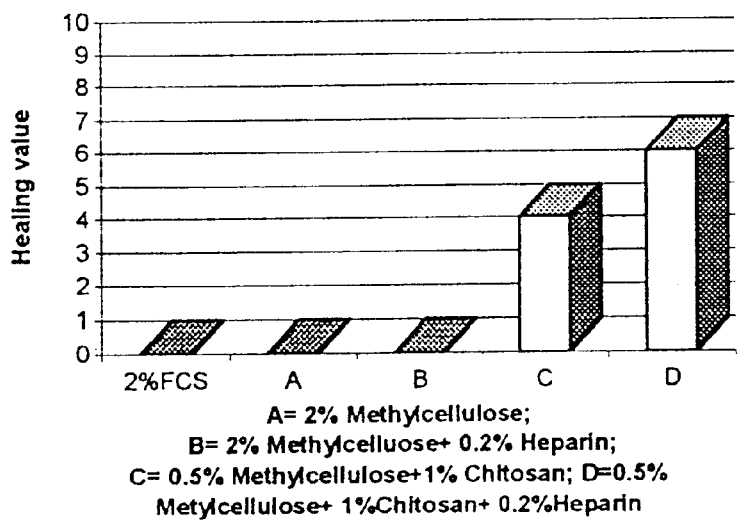

Healing after treatment of in vitro wounds with different gel compositions

A= 2% Methylcellulose;
B= 2% Methylcelluose+ 0.2% Heparin;
C= 0.5% Methylcellulose+1% Chitosan; D=0.5% Metylcellulose+ 1%Chitosan+ 0.2%Heparin

AGENTS, AND METHODS EMPLOYING THEM, FOR THE PREVENTION OR REDUCTION OF TISSUE ADHESION AT A WOUND SITE

This application is a continuation of application Ser. No. 08/513,777, filed on Aug. 8, 1995, now abandoned which is a 371 of PCT/SE95/00856, filed Jul. 13, 1995.

TECHNICAL AREA

The present invention relates to new anti-adhesion agents, i.e. products having the ability to prevent non-desired adhesion of tissues in connection with wound healing. The product has also the ability to improve healing quality by stimulating regeneration of tissue.

The invention also includes a process to prevent such undesired adhesion of tissues.

BACKGROUND OF THE INVENTION

Our ability to move freely as desired and according to the current need is of utmost importance for our life quality. Suitable function of the musculoskeletal system in close cooperation with mainly the skin, mucosal membranes and nervous tissue is a prerequisite for our ability to move and requires per se that different structures such as bone, muscles and tendons are freely moveable relative to each other. Such activities require sliding zones, minimal friction and maximized freedom to move. Sliding systems between for example adjacent muscles and tendons as well as between skin and adjacent tissues are thus required for optimal function. The same is true for visceral structures, such as the gastrointestinal tract, heart, lung, brain and spinal cord. The sliding systems are formed by thin sheets of loose connective tissue, which in the abdomen, thoracic cavity, pericardial space and for the brain and spinal cord are delimited by mesothelial cells. The paratenons show a similar design.

These sliding systems are very sensitive to inflammation and injury. Scar tissues is easily formed resulting in impaired function and even loss of function. Adhesions may be formed in the abdominal cavity, i.e. formation of strings, and membrane-like fusions of adjacent or surrounding structures may eventually result in ileus, a life threatening condition. Surgical procedures carried out to treat injuries, remove tumors or treat other disorders or for performing reconstructions always result in scar formation and thereby more or less comprehensive loss of "natural and original" sliding systems.

The healing of injuries to the skin and mucosal linings are complicated, on the one hand by the restricted ability of connective tissue to regenerate and on the other hand by the formation of immature granulation tissue, which latter tissue has a limited capacity to gain a maturity similar to that of normal tissue. Thus, the dermis is neither re-formed in youths nor in adults after injury with few exceptions. Small and/or superficial injuries to the dermis are healed by replacement of the lost tissue by generation of adjacent type like structures and by the generation of reactive granulation tissue. More extensive tissue losses, such as after deep burns, third degree thermal injuries, and after loss of part of the dermis inevitably heal with scar formation, variable but persistent loss of tissue and with permanent deformations. The mechanically resistant component in the scar tissue is largely constituted by the type III collagen of short fibres and inferior organisation and has therefore inferior mechanical properties as compared to collagen of the normal optimal type I. The fraction of amorphous plastic ground substance has been reduced as well as the tissue cellularity. The number of blood vessels is with time reduced in relation to that in normal tissue and the distribution and type of vessels have changed. Wide, thin-walled vessels of inferior function as compared to the corresponding normal blood vessels are frequent, as are abnormal lymph vessel systems. The sliding systems are thus eventually replaced by rigid, fibrous collagen connective tissue.

An additionally complicating, very important factor is created by the appearance of myofibroblasts, i.e. "common" connective tissue cells (fibroblasts) which, as well as a part of the macrophages, have an increased number of cytoplasmic bundles of muscle proteins which enable the cells to slowly and powerfully contract and maintain the contraction for a long period of time. This may result in contractures which further deform and limit the function of the affected tissue. An increased presence of myofibroblasts is seen for example around breast implants (silicon prosthesis implanted for breast enlargement or breast reconstruction; a more detailed description by C. Lossing & H-A Hansson is found in an article in Plastic Reconstr. Surgery 1993, Vol. 91, page 1277–1286) and around sutures and other implants of foreign materials. Myofibroblasts are prevailing at an increased frequency around joints in certain rheumatoid diseases and may result in deviation of fingers and sometimes also in luxations. This cell is the pathogenic factor causing the deformities of the hand striking patients with Dupuytren's contracture. The myofibroblasts as well as common fibroblasts are attached to collagen threads by means of specific heterodimeric receptors, one unit of which always is constituted by β1-integrin. Blocking of integrins results in elimination of contractures. Inflammation reducing drugs may influence the expression of integrins.

Sliding systems in loose connective tissue with or without a well defined sliding surface thus only restore in cases with minimal inflammation. The formation of granulation tissue occur, however, only in conjunction with an inflammatory process which per se does result in formation of immature cells and tissue components. This inability of the new tissue formed during the repair process to approach the normal differentiation levels is the reason that scar tissue is of inferior quality quantitatively and qualitatively as compared to the original, mature but lost tissue. Maturation of regenerated tissue requires access to growth factors which control and promote differentiation of cells, fibres and ground substance.

BACKGROUND ART

Extensive research has been directed to solve the problem of avoiding undesired adhesion of tissues in connection with the healing of wounds, for example wounds caused by surgical incisions, by accident, inflammations and tumors. PCT application No. US90/02406 describes technology associated with this specific problem and also includes a relatively extensive elucidation of the background art. The techniques described in said patent application are based on the use of sandwich constructions comprising a biodegradable bioactive membrane, the opposed surfaces of which have different composition and thereby different biological functions. However, the corresponding products do not seem to be available on the market.

SUMMARY OF THE INVENTION

Accordingly, the present invention has for an object to provide an anti-adherence agent with the use of which there is induced only a minimal inflammation of short duration, said agent being, moreover, bioacceptable and biodegradable without resulting in interfering degradation products.

Another object of the invention is to provide an anti-adherence agent having the ability to induce interface surfaces and resulting in simplified mechanical and technical handling in connection with for example surgical incisions.

Yet another object of the invention is to provide a process to prevent or substantially reduce undesirable adhesion of adjacent or surrounding tissues and organs in connection with wound healing.

A further object of the invention is to stimulate regeneration of tissue in connection with wound healing.

For these and other objects which will be elucidated by the following disclosure there is provided through the present invention a new use of chitosan and a polysaccharide immobilized thereto, said polysaccharide being selected from heparin, heparan sulfate, and dextran sulphate. While using this composition of matter there can be produced an agent having the ability to eliminate or substantially reduce undesirable adhesion of damaged tissue to adjacent or surrounding tissues in connection with wound healing.

The polysaccharide used can be immobilized to the chitosan in mainly three different ways. Thus, immobilization can take place by ionic binding, by covalent binding or by mechanical inclusion in the chitosan in connection with precipitation from solution. A process for covalent binding of the relevant polysaccharide to a substrate carrying amino groups is described in U.S. Pat. No. 4,613,665.

As a polysaccharide it is particularly preferred to use heparin or heparan sulphate said substances being commercially available on the market from several manufacturers. Also partly hydrolyzed forms of the polysaccharide can, of course, be used provided that the biological activity is maintained.

The anti-adherence agent used in accordance with the invention can be present in different physical forms, for example as films or membranes, gels, tubes or hoses, powders, aerosols or solutions. The relevant form is, of course, adapted to the damage involved. In most cases films are useful, whereas tubes or gels can be used in special cases, for example in connection with elongate confined tissues, such as muscles and tendons.

Chitosan is a linear 1,4-bound polysaccharide built up from β-D-glucose amine units. The chitosan is manufactured by N-deacetylation of chitin, a polymer forming the shell of inter alia insects and shellfish. Commercially, chitin is recovered from crab and shrimp shells which constitute waste products from the fishing industry. By controlling the alkaline treatment of chitins chitosans of varying degree of N-acetylation can be made. When treating chitin with concentrated alkali, usually sodium hydroxide, N-deacetylation thus takes place, i.e. acetamido groups are converted into amino groups to form chitosan.

The physical properties of chitosan affecting its usefulness depend on the degree of N-acetylation, the molecular weight and the homogeneity. Chitosan is bio-degradable, both by chitinase in the digestive system and by lysozyme and other enzymes in the body liquids.

It is preferred in connection with the use of the present invention that the chitosan has a degree of N-acetylation of at most about 90% and preferably at most about 50%. It is particularly preferred that the degree of N-acetylation is less than about 25%.

The present invention also provides for a process to prevent or substantially reduce undesirable adhesion of tissues in connection with wound healing. This process involves applying at the site of the wound healing an agent comprising chitosan and a polysaccharide immobilized thereto selected from heparin, heparan sulphate and dextran sulphate.

Depending on the character of the wound involved the agent can be applied in the form of a film, in the form of a gel or in the form of a tube or a hose. The product to be selected for the application can easily be decided in connection with for example the relevant surgical procedure.

EXAMPLES OF PREFERRED EMBODIMENTS

The present invention will in the following be illustrated in connection with non-limiting examples. In the examples all films have been prepared in Petri dishes having a surface area of 54 $cm^2$.

EXAMPLE 1

Preparation of Chitosan Film 5 g hydrochloride salt of chitosan (50% degree of acetylation, Pronova) are dissolved in distilled water (0.5 L, 1% v/w). 10 mL of the solution obtained are transferred to a Petri dish, and a film of chitosan is formed by e aporation and drying in a heating cabinet at 70° C. for 24 h. The film obtained is then neutralized by the addition of a sodium phosphate buffer, 0.2 M, pH 9.0. The film is allowed to remain in the Petri dish in said buffer at room temperature for 2–4 h, is then washed 3–4 times with water and allowed to dry.

EXAMPLE 2

Preparation of Chitosan Film 5 g hydrochloride salt of chitosan (20% degree of acetylation, Pronova) are dissolved in a 2% acetic acid solution (0.5 L, 1% v/w). The solution is autoclaved for 1 h at 125° C. for sterilization purposes. After cooling a film is made in a Petri dish, in this case with the use of 20 mL of the solution. The film is then allowed to dry at room temperature and neutralized by the addition of a sodium phosphate buffer, 0.2 M, pH 9.0, added to the dish. The film is allowed to stay in this buffer for 2–4 h at room temperature, is then washed with distilled water 3–4 times and again allowed to dry.

EXAMPLE 3

Nitrous Acid Degradation of Heparin

One gram of heparin is dissolved in 300 mL of water. The solution is cooled to 0° C. in ice water and maintained cold. First 10 mg of sodium nitrite ($NaNO_2$) is added. Then 2 mL of acetic acid is added to the solution while stirring. The reaction mixture is maintained at 0° C. for two hours, dialyzed, and freeze dried. The yield is 0,7 g degraded heparin.

EXAMPLE 4

Periodate Oxidation of Heparin

A solution of sodium periodote-oxidized sodium heparin is prepared in the following manner. One gram of sodium periodote, $NaIO_4$, is dissolved in 200 mL of distilled water. Ten grams of sodium heparin is added to the solution of sodium periodate and is stirred over night in the dark. The resulting solution, after adding 10 mL of glycerol and stirring for two hours, is dialyzed against water. The water is exchanged every hour. This results in a solution containing periodate-oxidized heparin in a concentration of about 19 mg/mL.

EXAMPLE 5

Preparation of Chitosan Film with Covalently Bonded Heparin (End-Point Attachment)

To a neutralized chitosan film prepared in accordance with Example 1 there are added 20 mL of a solution containing 125 mg nitrite-degraded heparin, prepared as in Example 3, dissolved in 0.5 L water and containing 4.4 g NaCl. To the solution is added 15 mg sodium cyanoborohydride. The pH of the solution is adjusted to 3.9 using 0.5 M hydrochloric acid or another acid. The solution containing the chitosan film is allowed to stand at room temperature for 14 h, and the treated film is then washed 3–4 times with water and is allowed to dry.

EXAMPLE 6

Preparation of Chitosan Film with Covalently Bonded Heparin (Multi Point Attachment)

A neutralized chitosan film prepared in accordance with Example 2 is allowed to stay for 24 h in 20 mL of the following solution. 4.4 sodium chloride and 125 mg periodate-oxidized heparin, prepared as described in Example 4, are dissolved in 0.5 L of water, the pH is adjusted to 3.9 using 0.5 M hydrochloric acid. To the solution there is added 15 mg sodium cyanoboro-hydride, and the solution is kept for 10 hours at room temperature. The treated film is then washed with water 3–4 times and allowed to dry. With regard to details concerning this technique of covalent binding of heparin reference is made to the above-mentioned U.S. Pat. No. 4,613,665.

EXAMPLE 7

Preparation of Chitosan Film with Tonically Bonded Heparin.

A neutralized chitosan film is prepared as in Example 2. A solution of heparin (125 g in 0.5 L water containing 4.4 g NaCl) is added. After 3 hours at room temperature the film is rinsed with 2×0.5 L water and dried.

EXAMPLE 8

Biological Test, Control

The film prepared in accordance with Example 2 is used as an anti-adherence membrane in the following animal model. The abdominal wall of a rat is opened and on each side of the sagittal line there is produced in a surgical manner a wound about 12×10 mm. One defect is covered with a film from Example 2, a piece of about 18×15 mm, whereas as the other defect is left open. The membrane is sutured using Dexon® 7-0 in such a manner that no suture is exposed in the abdominal cavity.

The result is evaluated after 2 and 4 weeks. In this connection modest adherences in the abdominal cavity against the membrane are observed, whereas massive adherences could be demonstrated if the tissue defect is not covered by a film.

The abdominal defect beneath the film heals essentially with scar tissue formation, and there are signs of inflammatory reaction and capsule formation around the film.

EXAMPLE 9

Biological Test, in Accordance with the Invention

The film made in accordance with Example 3 is used as an anti-adherence membrane in the following animal model.

The abdominal wall of a rat is opened and on each side of the sagittal line there is created in a surgical manner a wound of about 12×10 mm.

One defect is covered with film, about 18×15 mm, whereas the other defect is left open. The membrane is sutured in the same manner as in Example 8.

The wound area left open displayed several adherences in contrast to the wound covered by the film, which had very few if any adherences.

EXAMPLE 10

Preparation of Chitosan Film with Ionically Bonded Heparin 5 g hydrochloride salt of chitosan (45% degree of acetylation, Pronova) are dissolved in water (0.5 L, 1% v/w). The solution is autoclaved for 1 h at 125° C. for sterilization purposes. After cooling a film is made in a Petri dish, in this case with the use of 20 mL of the solution. The film is then allowed to dry at room temperature and a solution of heparin (125 g in 0,5 L water) is added. After 3 hours at room temperature the film is rinsed with 2×0.5 L water and dried.

EXAMPLE 11

Preparation of Chitosan Film 5 g hydrochloride salt of chitosan (45% degree of acetylation, Pronova) are dissolved in water (0.5 L, 1% v/w). The solution is autoclaved for 1 h at 125° C. for sterilization purposes. After cooling a film is made in a Petri dish, in this case with the use of 20 mL of the solution. The film is then allowed to dry at room temperature and neutralized by the addition of a sodium phosphate buffer, 0.2 M, pH 9.0, added to the dish. The film is allowed to stay in this buffer for 2–4 h at room temperature, is then washed with distilled water 3–4 times and again allowed to dry.

EXAMPLE 12

Biological Test, in Accordance with the Invention

Films prepared from chitosan-heparin as described above in Example 10 are positioned to cover wounds (10×12 mm, depth 1 mm) prepared on the parietal abdominal wall as described above. An identical wound is prepared on the contralateral side of the abdominal wall, and covered by a Chitosan film as described in Example 11. The occurrence of adherence formation is evaluated after 2 weeks. The wound covered by the heparin-chitosan film lacks adherences while that covered by the plain chitosan film shows a few, minor adherences. Light microscopic examination of the heparin-chitosan film reveals improved healing of the wound, including the extent of covering by mesothelial-like cells, and that there is a less extensive infiltration of inflammatory cells at the interface between the heparin-chitosan film and the wounded abdominal wall tissue than in corresponding area covered by the plain chitosan film.

EXAMPLE 13

Preparation of Chitosan-Heparin Films 5 g hydrochloride salt of chitosan (16% degree of acetylation, Pronova) are dissolved in a 2% acetic acid solution (0.5 L, 1% v/w). The solution is autoclaved for 1 h at 125° C. for sterilization purposes. After cooling a film is made in a Petri dish, in this case with the use of 20 mL of the solution. The film is then allowed to evaporate in an oven at 70° C. for 16 h. The film is treated with a 0.1 M NaOH solution for 3 h at room temperature and then washed with distilled water 3–4 times and again allowed to dry in 70° C. for 2 h. The resulting film is then transferred to a Petri dish and 30 mL of a sterile solution of native heparin (1% w/v, pig mucosa, Kabivitrurn) in 0.2 M phosphate buffer (pH 6.4) is added. The film is kept at room temperature overnight and then rinsed with sterile water and dried in a LAF bench. Four more films are prepared as above with the modification that they are treated with 0.5%, 0.1%, 0.01% and 0.00% solutions of heparin respectively. The heparinized films are subjected to elemental analysis which shows that the films contain 1.2%, 0.9%, 1.3%, 0.23% and 0.00% sulfur, respectively. These values correspond to a heparin content of 9.2%, 7.7%, 10.8%, divided into six groups with ten biopsies 1.9% and 0* respectively.

EXAMPLE 14

Preparation of in Vitro Wounds

Sterile human skin is obtained from mastectomy specimens. In each experiment only skin from a single donor is used. Under sterile conditions, circles with a diameter of 6mm are cut with a biopsy punch (Stiefel Laboratories, UK). In the centre of each piece, on the epidermal side, a partial wound is made with a 3 mm biopsy punch and subsequently pieces are transferred to 12-well plates (Costar) with the epidermal side up. Each well is filled with Dulbeccos Modified Eagles Medium (DMEM) to the epidermal level keeping the wound in the gas/liquid interface. Fetal Calf serum, 2% (FCS) and antibiotics (penicillin 50 $\mu$g/mL and streptomycin 50 $\mu$g/mL) are added to all samples.

EXAMPLE 15

In Vitro Healing Test

The in vitro wounds, described in Example 14, are divided into five groups with ten biopsies in each group. Every wound is covered with a heparinized film as decribed in Example 13. The media are changed every day. After seven days the pieces are fixed in 4% neutral buffered formaldehyde, dehydrated through an ethanol-xylene series and embedded in paraffin. Cross sections, 10–20 mm in thickness are stained with haematoxylin and eosin and the degree of re-epithelialization is assessed by light microscopy. Only wounds totally covered with keratinocytes are regarded as healed.

As is evident from FIG. 1, films with a heparin content below 2% do not stimulate cell proliferation.

EXAMPLE 16

Preparation of Gel Compositions

Water containing 0.9% NaCl is used to prepare the following four gel compositions:
A=2% Methylcellulose
B=2% Methylcellulose+0.2% Sodium heparin
C=0.5% Methylcellulose+1% Chitosan (16% acetylation)
D=0.5% Methylcellulose+1% Chitosan (16% acetylation)+0.2% Sodium heparin

EXAMPLE 17

In Vitro Healing Test

The in vitro wounds, described in Example 14, are divided into six groups with ten biopsies in each group. Every wound in five of the groups are covered with a gel composition as decribed in Example 16. The last group is only treated with the media (2% FCS). The media are changed every day. After seven days the pieces are fixed in 4% neutral buffered formaldehyde, dehydrated through an ethanolxylene series and embedded in paraffin. Cross sections, 10–20 mm in thickness are stained with haematoxylin and eosin and the degree of re-epithelialization is assessed by light microscopy. Only wounds totally covered with keratinocytes are regarded as healed.

As is evident from FIG. 2, a gel consisting of a combination of Chitosan and Heparin heals the wounds better than a gel with only Chitosan or only Heparin does.

EXAMPLE 18

Biological Test, in Accordance with the Invention

Example 9 is repeated using the film made in accordance with Example 7.

As is clear from the biological experiments described above the use of the techniques according to the present invention allows substantially improved healing properties in view of prevented adhesion and stimulated growth. The invention is not restricted to the examples given above and the scope of the invention is limited only by the scope of the appended claims.

With regard to the application of the invention there can be mentioned that films or membranes, gels or powders prepared as above or solutions can be used in connection with wounds and defects in or on the following organs and structures: abdominal wall; thorax wall; lung; heart-pericardium; central vessels; intestinal tract; urogenital tract; skull; cerebral meninges; spinal cord; tendons; nerves; muscles; bone; mucosa; cornea, skin etc.

Products in the form of tubes or hoses or gels can be used as guides in stimulated growth and concurrently gliding surfaces can be maintained by the fact that adhesion to the environment is avoided. Such products can be used in connection with nerves, tendons and ligaments, intestinal tract, urogenital tracts, blood vessels etc.

Even better stimulation of healing quality can probably be achieved by a combination of this invention with growth factors.

What is claimed is:

1. A method for preventing or reducing undesirable adhesion of tissues in connection with wound healing and for stimulating regeneration of tissue at a wound site, comprising the step of applying at the wound site an agent comprising chitosan and heparin immobilized to the chitosan, with the heparin being present in a content which is greater than 1.9% by dry weight and in an amount sufficient to prevent or reduce undesirable tissue adhesion and stimulate tissue regeneration.

2. A method according to claim 1, wherein the chitosan has a degree of N-acetylation of no more than about 90%.

3. A method according to claim 1 or 2, wherein the agent is applied in the form of a film or membrane.

4. A method according to claim 1 or 2, wherein the agent is applied in the form of a gel.

5. A method according to claim 1 or 2, wherein the agent is applied in the form of a tube or a hose.

6. A method according to claim 1 or 2, wherein the agent is applied in the form of a powder, an aerosol or a solution.

7. A method according to claim 1 or 2, wherein the heparin is immobilized to the chitosan by means of ionic bonds.

8. A method according to claim 1 or 2, wherein the heparin is immobilized to the chitosan by means of covalent bonds.

9. A method according to claim 1 or 2, wherein the heparin is immobilized to the chitosan by means of mechanical inclusion.

10. An agent for preventing or reducing undesirable adhesion of tissues in connection with wound healing and for stimulating regeneration of tissue at a wound site, which comprises chitosan and heparin immobilized to the chitosan, with the heparin being present in a content which is greater than 1.9% by dry weight and in an amount sufficient to prevent or reduce undesirable tissue adhesion and stimulate tissue regeneration.

11. An agent according to claim 10, wherein the chitosan has a degree of N-acetylation of no more than about 90%.

12. An agent according to claim 10 or 11 in the form selected from the group consisting of a film, a membrane, a gel, a tube, a hose, a powder, an aerosol and a solution.

13. An agent according to claim 10 or 11, wherein the heparin is immobilized to the chitosan by means selected from the group consisting of ionic bonds, covalent bonds and mechanical inclusion.

* * * * *